US012806240B2

(12) United States Patent
Lux et al.

(10) Patent No.: US 12,806,240 B2
(45) Date of Patent: Nov. 24, 2026

(54) AQUEOUS EXTRACTION OF CANNABINOIDS

(71) Applicant: Curaleaf, Inc., New York, NY (US)

(72) Inventors: Andrew Lux, Tabernacle, NJ (US); Robert Scott Winnicki, Auburndale, MA (US)

(73) Assignee: Curaleaf, Inc.

( * ) Notice: Subject to any disclaimer, the term of this patent is extended or adjusted under 35 U.S.C. 154(b) by 360 days.

(21) Appl. No.: 18/588,403

(22) Filed: Feb. 27, 2024

(65) Prior Publication Data

US 2024/0285705 A1 Aug. 29, 2024

Related U.S. Application Data

(60) Provisional application No. 63/449,012, filed on Feb. 28, 2023.

(51) Int. Cl.

| | |
|---|---|
| ***A61K 36/00*** | (2006.01) |
| ***A61K 31/00*** | (2006.01) |
| ***A61K 36/185*** | (2006.01) |

(52) U.S. Cl.

CPC .......... *A61K 36/185* (2013.01); *A61K 31/658* (2023.05); *A61K 2236/33* (2013.01); *A61K 2236/333* (2013.01); *A61K 2236/39* (2013.01); *A61K 2236/53* (2013.01)

(58) Field of Classification Search

CPC .................................................. A61K 2236/39

See application file for complete search history.

(56) References Cited

U.S. PATENT DOCUMENTS

| | | | |
|---|---|---|---|
| 11,208,393 B2 | 12/2021 | Durst et al. | |
| 2015/0038567 A1 | 2/2015 | Herkenroth et al. | |
| 2019/0359550 A1* | 11/2019 | Wohleb .................. | C07C 51/43 |

FOREIGN PATENT DOCUMENTS

| | | | |
|---|---|---|---|
| CN | 111039762 A | 4/2020 | |
| CN | 111039762 B | 9/2022 | |
| MA | 37112 A1 | 1/2016 | |
| WO | WO 2020028198 A1 | 2/2020 | |

OTHER PUBLICATIONS

International Search Report and Written Opinion in International Appln. No. PCT/US2024/017508, mailed on Sep. 10, 2024, 18 pages.

Invitation to Pay Additional Fees and, Where Applicable, Protest Fee in International Appln. No. PCT/US2024/017508, mailed on May 27, 2024, 10 pages.

* cited by examiner

*Primary Examiner* — Qiuwen Mi

(74) *Attorney, Agent, or Firm* — Fish & Richardson P.C.

(57) ABSTRACT

The present disclosure provides, in some embodiments, methods for aqueous extraction of cannabinoids from cannabis plant material.

11 Claims, 6 Drawing Sheets

AQUEOUS EXTRACTION OF CANNABINOIDS

CROSS-REFERENCE TO RELATED APPLICATIONS

This application claims the benefit of U.S. Provisional Patent Application No. 63/449,012, filed Feb. 28, 2023. The contents of this application are incorporated herein by reference in its entirety.

FIELD OF THE INVENTION

The subject matter disclosed herein generally relates to methods for aqueous extraction of cannabinoids.

BACKGROUND OF THE INVENTION

Conventional methods for extracting cannabinoids from cannabis plant use organic solvents (e.g., hexane, heptane, butane, propane, dichloromethane, ethyl acetate), alcohols (e.g., ethanol, methanol), and high pressure gases (e.g., supercritical $CO_2$). These reagents are costly and they create a safety risk. Explosion proof and flammable resistant processing equipment may be used and large scale solvent recycling systems may be employed to reduce environmental impact. It is therefore of interest to develop new methods for extracting cannabinoids from cannabis plant that are low cost, safe, and environmentally friendly.

SUMMARY OF THE INVENTION

The present disclosure concerns novel and non-obviousness methods for extracting cannabinoids from cannabis plants. Aspects of the present disclosure provide a method for aqueous extraction of cannabinoids from cannabis plant comprising (a) contacting cannabis plant material with an aqueous base solution for a time and under conditions sufficient for extraction of one or more cannabinoids from the cannabis plant material into the aqueous base solution; (b) collecting the aqueous base solution comprising the one or more cannabinoids; (c) adding an aqueous amine solution to the aqueous base solution to produce one or more acidic cannabinoid-amine salts.

In some embodiments, the ratio of cannabis plant material and the aqueous base solution is between 1:2 to 1:20 (w/v). In some embodiments, the ratio of cannabis plant material and the aqueous base solution is 1:10 (w/v).

In some embodiments, the aqueous base solution is selected from the group consisting of an aqueous sodium hydroxide solution, an aqueous potassium hydroxide solution, an aqueous calcium hydroxide solution, an aqueous ammonium hydroxide solution, an aqueous sodium bicarbonate solution, an aqueous potassium bicarbonate solution, an aqueous sodium carbonate solution, and an aqueous potassium carbonate solution. In some embodiments, the aqueous base solution is the aqueous sodium hydroxide solution. In some embodiments, the concentration of the aqueous base solution is between 0.1 to 0.6 M. In some embodiments, the concentration of the aqueous base solution is 0.3 M. In some embodiments, steps (a) and (b) are repeated from 2 to 6 times using fresh aqueous base solution.

In some embodiments, the aqueous amine solution is selected from the group consisting of an aqueous dimethylethanolamine (DMEA) solution, an aqueous dicyclohexylamine solution, an aqueous piperidineethanol solution, an aqueous tetramethylethylenediamine (TMEDA) solution, an aqueous 1,8-diazabicyclo[5.4.0]undec-7ene (DBU) solution, an aqueous 1,5-diazabicyclo[4.3.0]non-5-ene (DBN) solution, an aqueous 1,4-diazabicyclo[2.2.2]octane (DABCO) solution, an aqueous N,N-diisopropylethylamine solution, and an aqueous quinine solution.

In some embodiments, methods described herein further comprise (c) adding an aqueous acid solution to the aqueous base solution to produce a precipitate comprising the one or more cannabinoids; and (d) collecting the precipitate comprising the one or more cannabinoids.

In some embodiments, the aqueous acid solution is added to the aqueous base solution in an amount sufficient to adjust the pH to between 4.5 and 1.5. In some embodiments, the aqueous acid solution is selected from the group consisting of an aqueous hydrochloric acid solution, an aqueous sulfuric acid solution, and an aqueous formic acid solution. In some embodiments, prior to step (c), the aqueous base solution is centrifuged, filtered, or both centrifuged and filtered. In some embodiments, the precipitate comprising the one or more cannabinoids is collected by centrifugation, filtration, or both centrifuged and filtered.

In some embodiments, methods described herein further comprise (e) dissolving the precipitate comprising the one or more cannabinoids in an ethanol solution and purifying the one or more cannabinoids from the ethanol solution. In some embodiments, the one or more cannabinoids are purified from the ethanol solution by evaporation, distillation, hydrophobic affinity chromatography, or a combination thereof. In some embodiments, the hydrophobic affinity chromatography is performed using a polydivinylbenzene resin.

Aspects of the present disclosure provide a method for continuous aqueous extraction of cannabinoids from cannabis plant comprising circulating an aqueous base solution between a first stirred-tank reactor and a second stirred-tank reactor, wherein the first stirred-tank reactor comprises cannabis plant material and the second stirred-tank reactor comprises a hydrophobic chromatography resin, and wherein the aqueous base solution is circulated for a time and under conditions sufficient for extraction of one or more cannabinoids from the cannabis plant material into the aqueous base solution and for the one or more cannabinoids in the aqueous base solution to bind to the hydrophobic chromatography resin.

In some embodiments, the ratio of cannabis plant material and the aqueous base solution is between 1:2 to 1:20 (w/v). In some embodiments, the ratio of cannabis plant material and the aqueous base solution is 1:10 (w/v). In some embodiments, the aqueous base solution is selected from the group consisting of an aqueous sodium hydroxide solution, an aqueous potassium hydroxide solution, an aqueous calcium hydroxide solution, an aqueous ammonium hydroxide solution, an aqueous sodium bicarbonate solution, an aqueous potassium bicarbonate solution, an aqueous sodium carbonate solution, and an aqueous potassium carbonate solution. In some embodiments, the aqueous base solution is the aqueous sodium hydroxide solution. In some embodiments, the concentration of the aqueous base solution is between 0.1 to 0.6 M. In some embodiments, the concentration of the aqueous base solution is 0.3 M.

In some embodiments, methods described herein further comprise washing and drying the hydrophobic chromatography resin.

In some embodiments, methods described herein further comprise eluting the one or more cannabinoids from the hydrophobic chromatography resin into an ethanol solution.

In some embodiments, methods described herein further comprise purifying the one or more cannabinoids from the ethanol solution. In some embodiments, the one or more cannabinoids are purified from the ethanol solution by acid precipitation, evaporation, distillation, hydrophobic affinity chromatography, or a combination thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
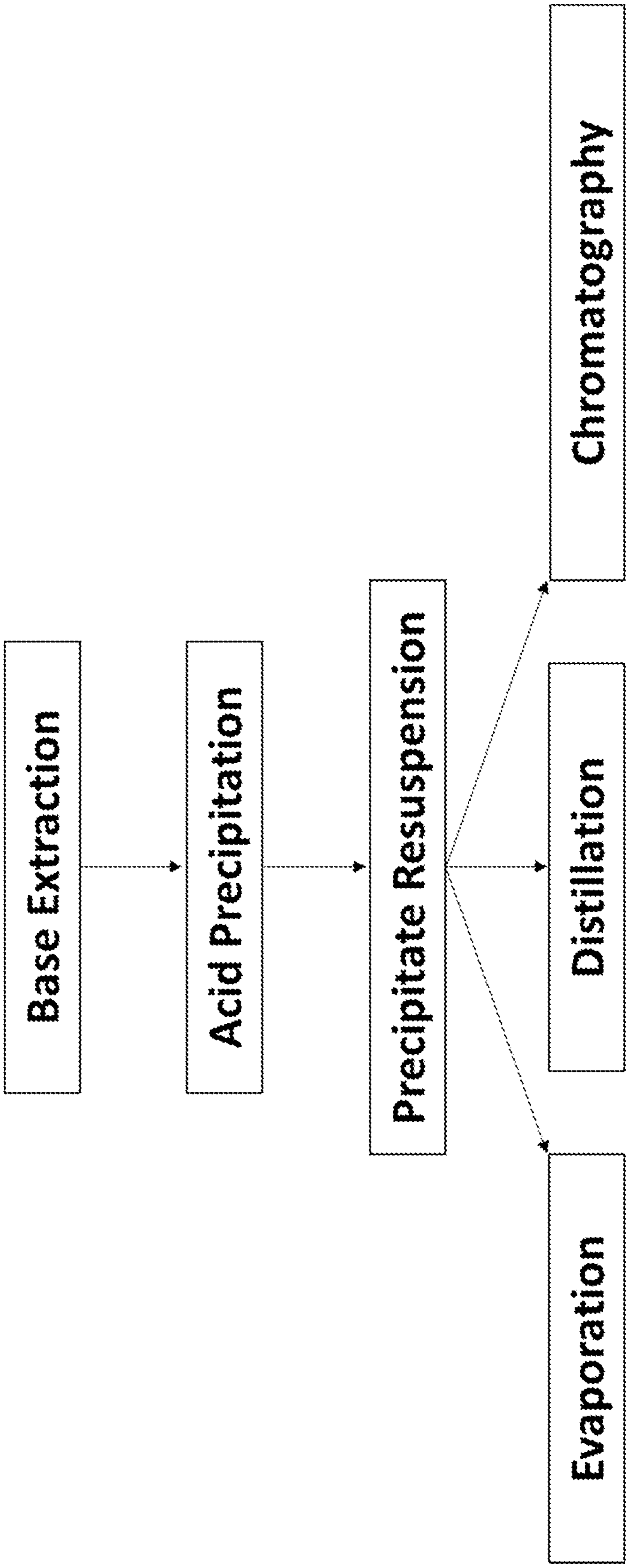
FIGS. 1A-1C include flow charts illustrating an aqueous cannabinoid extraction (ACE) process in accordance with some embodiments of the technology described herein.

The present disclosure is based, at least in part, on the development of methods for aqueous base extraction of cannabinoids from cannabis plant that provide several improvements over conventional approaches. Such improvements include:

(a) Reduced cost, safety risk, and environmental harm resulting at least in part from extraction of cannabinoids with aqueous solutions and without use of organic solvents.

(b) Improved yield resulting at least in part from highly efficient extraction of cannabinoids from plant material using aqueous base solutions that convert the carboxylic acids in cannabinoids to their alkali metal salts, thereby increasing aqueous solubility.

(c) Rapid and simplified extraction of cannabinoids resulting at least in part from methods that utilize wet cannabis plant material, and thus the need to dry cannabis plant material prior to extraction is avoided.

(d) Rapid and simplified extraction of cannabinoids resulting at least in part from methods that involve fewer processing steps (e.g., aqueous extraction performed without drying, milling, or post extraction pressing of plant material) and processing steps that are shorter in duration (e.g., aqueous extraction performed for 1 hour compared to supercritical $CO_2$ extraction performed for 6-8 hours) than has been conventional.

Accordingly, provided herein are substantially improved methods for extraction of cannabinoids from cannabis plant material. The methods described herein use aqueous base solutions that convert carboxylic acids in cannabinoids to their alkali metal salts, thereby increasing the aqueous solubility of cannabinoids. Once extracted from the plant material, cannabinoids in the aqueous base solution can be purified using a various methods including acid precipitation, affinity chromatography, distillation, evaporation, or a combination thereof. Thus, described herein are methods referred to as aqueous extraction of cannabis (AEC) that involve aqueous extraction of cannabinoids from the cannabis plant. Such methods described herein produced cannabinoids at a purity of >99% total cannabinoid content or a purity of >98% individual cannabinoids (e.g., delta-9-tetrahydrocannabinol ($\Delta^9$-THC), tetrahydrocannabinolic acid (THCA)).

There are at least 100 cannabinoids in a cannabis plant that may be extracted using the methods described herein, with tetrahydrocannabinol (THC) (e.g., $\Delta^9$-THC), delta-8-tetrahydrocannabinol ($\Delta^8$-THC)) being the most notable due to its psychoactive effects. Non-limiting examples of cannabinoids include tetrahydrocannabinolic acid (THCA), THC, cannabidolic acid (CBDA), cannabidiol (CBD), cannabinol (CBN), cannabigerol (CBG), cannabichromene (CBC), tetrahydrocannabivarin (THCV), and cannabidivarin (CBDV).

The cannabis plant material that can be used in the methods described herein include cannabis plant material with cannabinoids such as cannabis plant or plant parts (e.g., leaves, flowers, stems, and combinations thereof), or a combination thereof. Cannabis plant material includes wild-type plant, variants, hybrids, or combinations thereof.

Cannabis plant material having low cannabinoid content can be used in methods described herein. For example, methods described herein can be used to produce cannabinoids from cannabis plant having <5% total cannabinoid content, <4% total cannabinoid content, <3% total cannabinoid content, or <2% total cannabinoid content.

METHODS FOR AQUEOUS EXTRACTION OF CANNABINOIDS

To practice methods described herein, cannabis plant material is brought into contact with an aqueous base solution for a time and under conditions sufficient for extraction of cannabinoids from the cannabis plant material and into the aqueous base solution. Cannabinoids in the aqueous base solution can then be purified.

As used herein, the term "contact" or "contacting" in connection to plant material and a solution refers to an exposure of cannabis plant material with the aqueous base solution for a period sufficient for extraction of cannabinoids from cannabis plant material and into the aqueous base solution.

For example, as illustrated in FIG. 1A, methods described herein can include extracting cannabinoids from cannabis plant material using an aqueous base solution and then adding an aqueous acid solution to the aqueous base solution to form a precipitate comprising the cannabinoids. The resulting precipitate can be resuspended (e.g., in ethanol or acetone) and cannabinoids can then be purified by chromatography, distillation, evaporation, or a combination thereof.

Figure 1B:
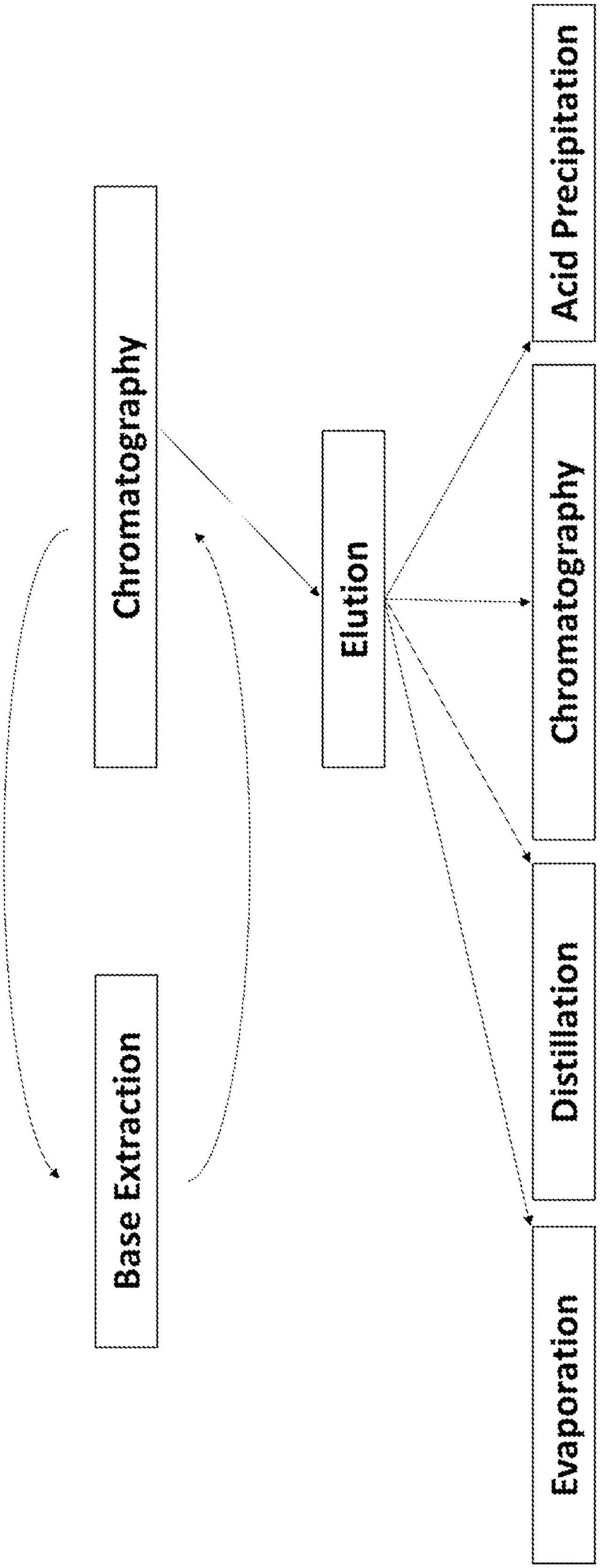

In another example, as illustrated in FIG. 1B, methods described herein can include extracting cannabinoids from cannabis plant material into an aqueous base solution and simultaneously purifying the cannabinoids from the aqueous base solution by absorption onto a chromatography resin (e.g., by fluidized bed absorption using an affinity chromatography resin). In such instances, cannabinoids can be eluted from the chromatography resin and further purified using evaporation, distillation, chromatography, recrystallization, or a combination thereof.

Figure 1C:
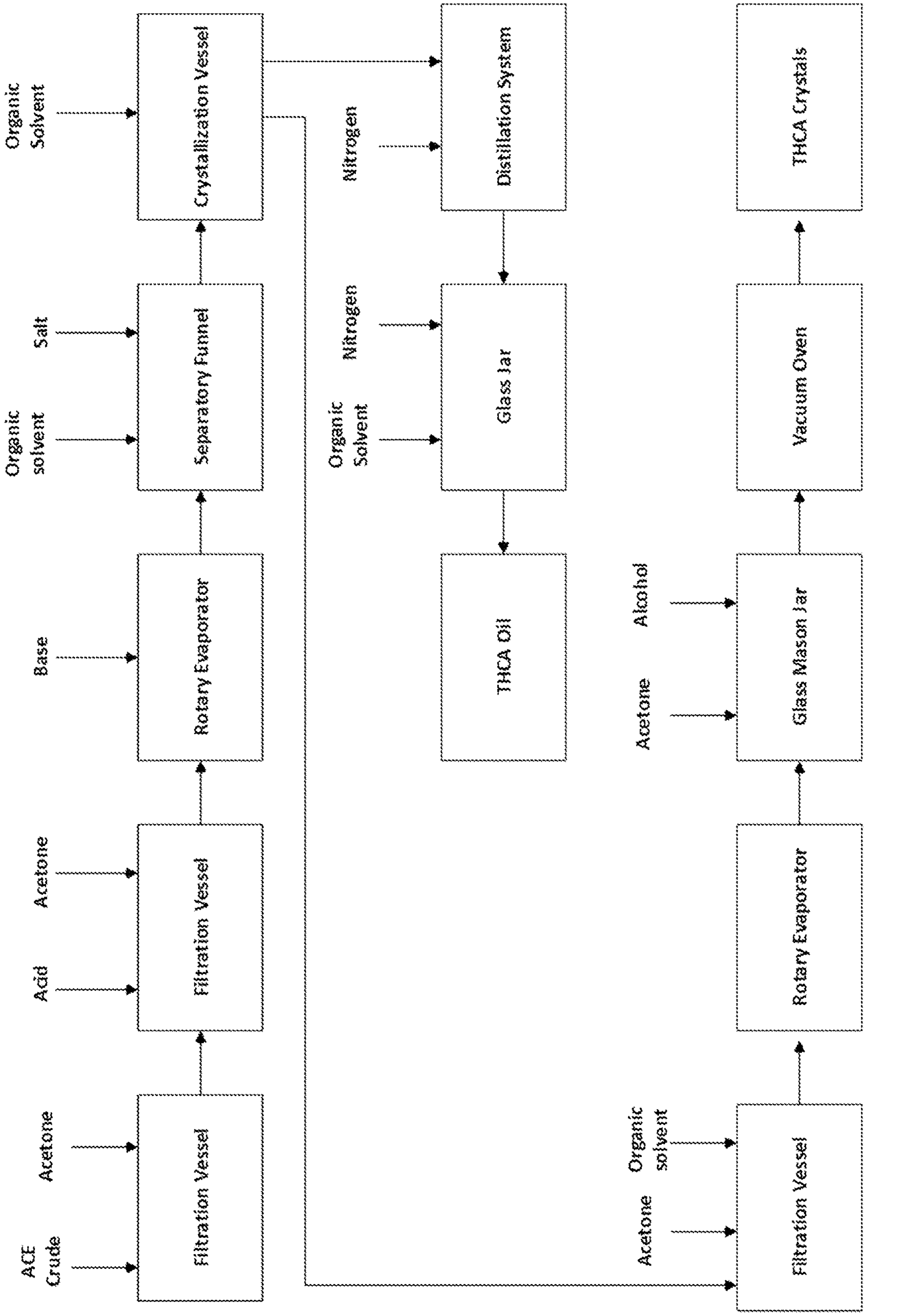

As shown in FIG. 1C, cannabinoids extracted from cannabis plant material using aqueous extraction methods described herein can be further separated and purified to yield cannabinoid oil and/or cannabinoid crystals, e.g., THCA oil and/or THCA crystals. In such instances, as shown in FIG. 1C, the extracted cannabinoids are subjected to one or more of filtration, rotary evaporation, crystallization, and distillation to produce cannabinoid oil and/or cannabinoid crystals.

Figure 2A:
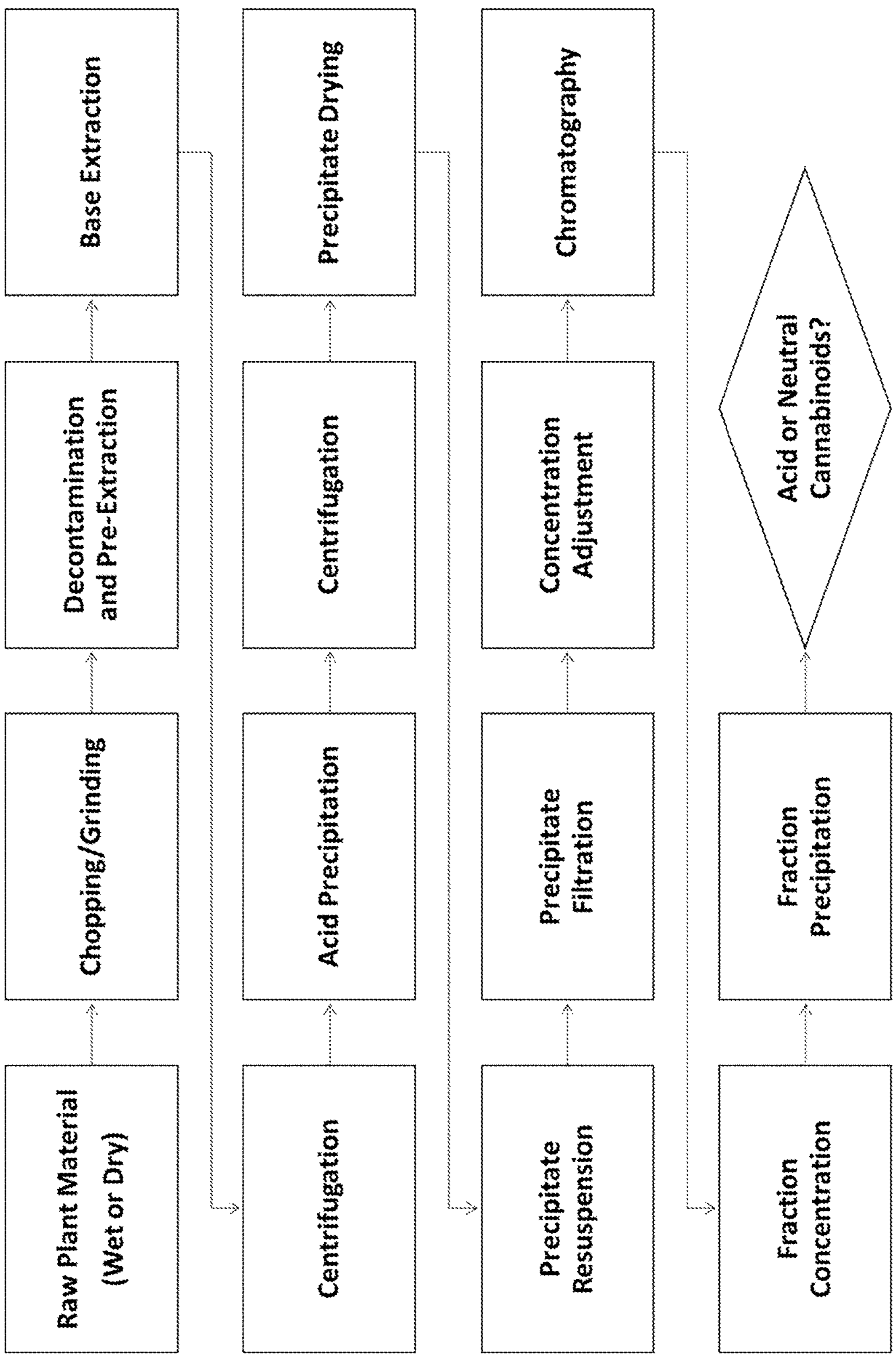
FIGS. 2A-2B include flow charts illustrating an ACE process in accordance with some embodiments of the technology described herein.
Figure 2B:
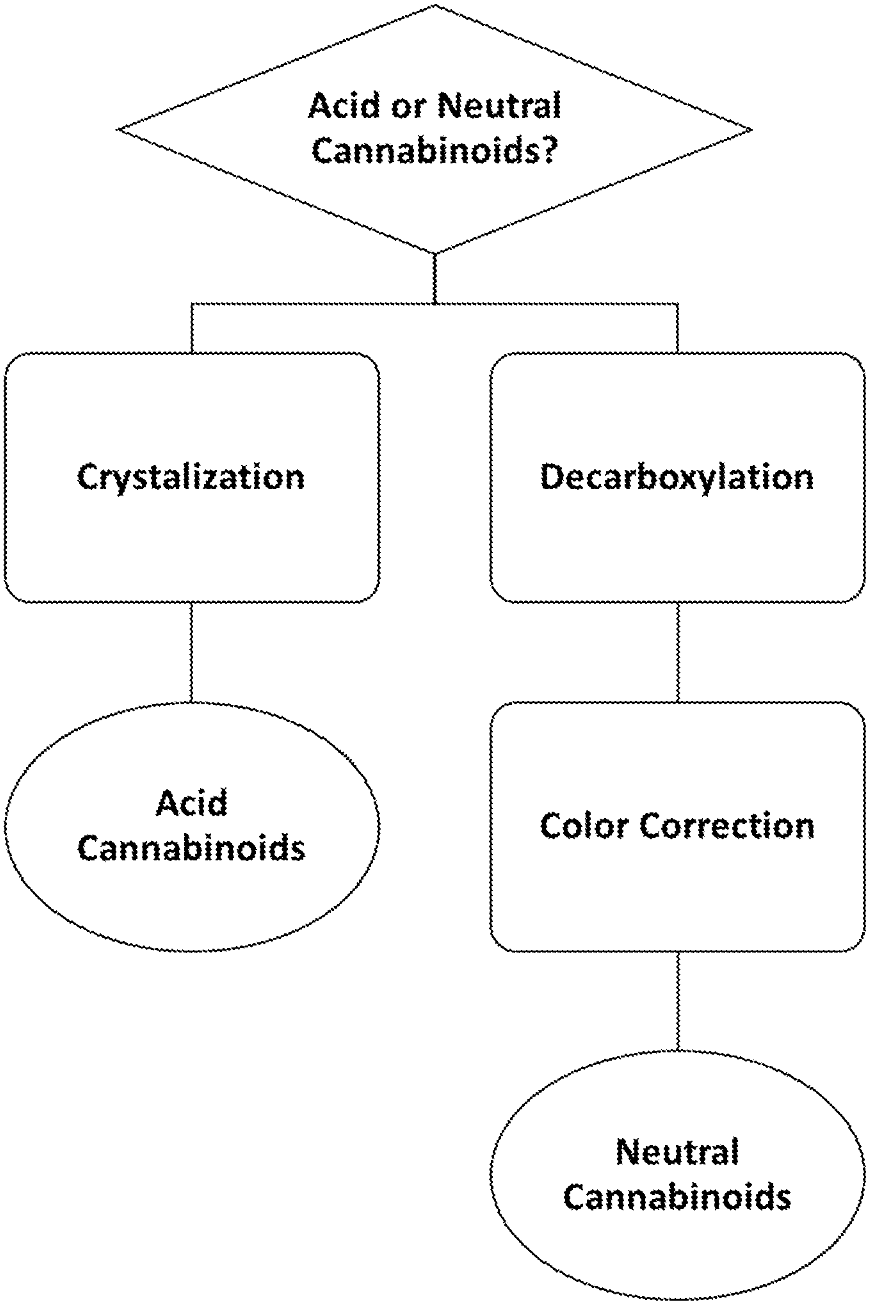

In another example, as illustrated in FIG. 2A, methods described herein can include extracting acid or neutral cannabinoids. In such instances, as illustrated in FIG. 2B, acid cannabinoids can be separated from mixture of acid and neural cannabinoids by crystallization and neutral cannabinoids can be separated from the mixture by decarboxylation.

Methods described herein are suitable for use for large scale or small scale extractions of cannabinoids from cannabis plant material. Accordingly, in some embodiments, methods comprise between 0.5-500 kg of cannabis plant material, e.g., between 0.5-250 kg, between 0.5-100 kg, between 0.5-50 kg, between 0.5-25 kg, between 0.5-5 kg, between 5-500 kg, between 25-500 kg, between 50-500 kg, between 100-500 kg, or between 250-500 kg.

Any ratio of cannabis plant material and aqueous base solution suitable for extracting cannabinoids from the cannabis plant material and into the aqueous base solution can be used in methods described herein. Suitable ratios include those suitable for conversion of the carboxylic acid moiety in a cannabinoid to its alkali salts and diffusion of the cannabinoid into the aqueous base solution. For example, the ratio of cannabis plant material and the aqueous base solution is between 1:2 to 1:20 (w/v), e.g., between 1:2 to 1:15 (w/v), between 1:2 to 1:10 (w/v), between 1:2 to 1:5 (w/v), between 1:5 to 1:20 (w/v), between 1:10 to 1:20 (w/v), or between 1:15 to 1:20 (w/v). These are non-limiting examples.

Various aqueous base solutions can be used in methods described herein for extracting cannabinoids from cannabis plant. As used herein, the term "an aqueous base solution" refers to an aqueous solution comprising a dissolved base, e.g., a strong base or a weak base. Non-limiting examples of aqueous base solutions for use in methods described herein include an aqueous sodium hydroxide solution, an aqueous potassium hydroxide solution, an aqueous calcium hydroxide solution, an aqueous ammonium hydroxide solution, an aqueous sodium bicarbonate solution, an aqueous potassium bicarbonate solution, an aqueous sodium carbonate solution, and an aqueous potassium carbonate solution.

Any concentration of aqueous base solution suitable for extracting cannabinoids from the cannabis plant material and into the aqueous base solution can be used in methods described herein. For example, the concentration of the aqueous base solution is between 0.1 to 0.6 M, e.g., between 0.1 to 0.5 M, between 0.1 to 0.4 M, between 0.1 to 0.3 M, between 0.1 to 0.2 M, between 0.2 to 0.6 M, between 0.3 to 0.6 M, between 0.4 to 0.6 M, or between 0.5 to 0.6 M.

Cannabis plant material can be in contact with the aqueous base solution for any amount of time suitable for extracting cannabinoids from the cannabis plant material and into the aqueous base solution. For example, cannabis plant material can be contacted with an aqueous base solution for at least 2 minutes, for at least 3 minutes, at least 4 minutes, at least 5 minutes, at least 6 minutes, at least 7 minutes, at least 8 minutes, at least 9 minutes, at least 10 minutes, at least 15 minutes, at least 30 minutes, at least 45 minutes, at least 1 hour, at least 1.5 hours, at least 2 hours, at least 2.5 hours, at least 3.0 hours, at least 3.5 hours, at least 4.0 hours, at least 4.5 hours, at least 5.0 hours, or more.

Methods described herein encompass using multiple aliquots or washes of aqueous base solution to achieve the desired level of cannabinoid extraction (e.g., removal of greater than 90% of cannabinoids from the cannabis plant material). For example, the aqueous base solution can be separated from the cannabis plant material and then fresh aqueous base solution is added. Separation of the aqueous base solution and addition of fresh aqueous base solution can be repeated one or more times (e.g., 2, 3, 4, 5, 6, 7, 8, 9, 10, or more times). In such instances, the aliquots of aqueous base solution can be pooled and cannabinoids extracted therefrom. In some examples, greater than 98% of cannabinoids from the cannabis plant material can be recovered from one wash of aqueous base solution. In other examples, greater than 98% of cannabinoids from the cannabis plant material can be recovered from two or three washes of aqueous base solution that have been pooled.

Methods described herein encompass separating plant material from the aqueous base solution using any separation technique known in the art including, but not limited to, sedimentation, filtration, centrifugation, screw pressing, and a combination thereof.

Aqueous base extraction of cannabinoids can be followed by purification of the extracted cannabinoids. Alternatively, or in addition to, aqueous base extraction and purification can occur simultaneously. In such instances, the aqueous base solution is continuously circulated such that it repeatedly contacts cannabis plant material and a separation resin (e.g., a hydrophobic affinity chromatography resin such as a polydivinylbenzene resin). An example of a method for continuous aqueous extraction of cannabinoids is described in Example 10.

Methods described herein can include purifying cannabinoids using various techniques including precipitation, chromatograph, evaporation, distillation, crystallization and combinations thereof.

When purifying cannabinoids from the aqueous base solution by acid precipitation, an aqueous acid solution can be added to the aqueous base solution to precipitate the cannabinoids. For example, to precipitate cannabinoids from an aqueous base solution, the aqueous acid solution can be added in an amount sufficient to adjust the pH to between about 4.5 and about 1.5, e.g., between 4.0 and 1.5, between 3.5 and 1.5, between 3.0 and 1.5, between 2.5 and 1.5, between 2.0 and 1.5, between 4.5 and 2.0, between 4.5 and 2.5, between 4.5 and 3.0, or between 4.5 and 3.5.

Various aqueous acid solutions can be used to precipitate cannabinoids in methods described herein. As used herein, the term "an aqueous acid solution" refers to an aqueous solution comprising a dissolved acid, e.g., a strong acid or a weak acid. Non-limiting examples of aqueous acid solutions for use in methods described herein include an aqueous hydrochloric acid solution, an aqueous sulfuric acid solution, and an aqueous formic acid solution.

Precipitation of the cannabinoids can be enhanced through the use of various flocking additives. Use of additives can greatly enhance the removal of cannabinoids from aqueous solutions by increasing particle size and neutralizing surface charges. Further, proper selection and blending of flocking additives can selectively precipitate cannabinoids leaving non-cannabinoid contaminates in the aqueous extract. Non-limiting examples of flocking additives include anionic polymers, cationic polymers, cellulosic polymers, colloidal clays, primary amines, secondary amines, tertiary amines, bicyclic amines, long chain polymers, anionic polymeric resins, cationic polymeric resin, modified silica resin, and combinations thereof.

Precipitate comprising the cannabinoids can then be collected using any method known in the art including, but not limited to, sedimenting, decanting, filtering, centrifuging, evaporating, decanting, and a combination thereof. In some examples, precipitate can be resuspended and/or dried using known methods for resuspending and drying precipitates. Non-limiting examples of methods for drying precipitates include air drying, IR enhanced evaporation, forced warm air drying, desiccation, and freeze drying.

Following drying, precipitate can be maintained at a temperature sufficient to maintain a dry precipitate. In some examples, precipitate can be maintained at a temperature between 37° C. and 50° C., e.g., precipitate can be maintained at a temperature of about 40° C., about 45° C., or about 50° C.

Methods described herein can include one or more resuspension steps in which precipitated cannabinoids are dissolved in a "green" solvent such as an alcohol (e.g., methanol, ethanol) or a ketone (e.g., acetone) and insoluble particulate can then be to removed, e.g., by sedimentation, filtration, centrifugation, or a combination thereof. Other organic solvents known to the art can be utilized such as straight chain hydrocarbons (e.g., pentane, hexane, heptane) and aromatic hydrocarbons (e.g., benzene, toluene, terpene, tetrahydrofuran (THF)). However, these "non-green" solvents are less desirable due to their toxicity, cost, and safety issues. Purified cannabinoids can then be obtained by solvent removal, e.g., solvent removal by evaporation, sedimentation, decanting, or a combination thereof. The solvent can be removed using any method known in the art such as evaporation or absorption on to solid state media. Resuspension, insoluble particulate removal, and solvent removal can be performed as many times as necessary to achieve the desired purity.

Methods described herein can include purifying cannabinoids using at least one chromatography step (e.g., affinity chromatography, flash chromatography, gas chromatography (GC), high-performance liquid chromatography (HPLC)). Any chromatography resin suitable for purifying one or more cannabinoids can be used in methods described herein. The chromatography resin can be utilized in any suitable arrangement (e.g., column chromatography, batch chromatography, or a combination thereof). In some examples, the chromatography resin is an affinity chromatography resin such as a hydrophobic interaction chromatography resin (e.g., a polydivinylbenzene resin, a styrene-divinylbenzene (DVB) resin, a poly(methyl methacrylate) (PMMA) resin, or a combination thereof).

Methods described herein can further compromise purification of acid cannabinoids by forming acid base pairs with other molecules, and removing these pairs from solution via sedimentation, precipitation, filtration, centrifugation or other techniques. Suitable functional groups for organic molecules are selected from a wide range of amines including primary amines, secondary amines, tertiary amines, and bicyclic amines. Non-limiting examples of amines include cyclohexlamine, dicyclohexamine (DHCA), and quinine. Non-limiting examples of amine polymers suitable for purification include functionalized acrylamides (e.g., poly(N-isopropyl acrylamide), poly(acrylamide-co-diallyldimethylammonium chloride)) and non-functionalize polyamines (e.g., poly(diallyl dimethyl ammonium chloride and poly-L-arginine) (PDADMAC). Suitable metal-polymer complexes include, but are not limited to, mono and divalent metals complexed with cyclodextrin.

Methods described herein can further comprise removal of the base from the acid base pair, thereby releasing a purified acid cannabinoid, without the need for traditional two phase separation. In some embodiments, the method is performed by dissolving the acid base pair in a suitable solvent (e.g., acetone or ethanol), acidifying the solvent with an acid (e.g., sulfuric acid or hydrochloric acid), and directly precipitating the resulting amine from solution. In another embodiment, the base is removed via dissolution in an appropriate solvent (e.g., ethanol) and the solution is passed through an anionic polymer resin. The resin binds the amine selectively, thereby releasing a purified acid cannabinoid.

Methods described herein can further comprise forming crystals of one or more cannabinoids using any suitable method and to any suitable purity. In some embodiments, the method comprises crystallization by mixing with solvent, rapid cooling, washing the crystals with a second solvent, and evaporation. In some embodiments, the method comprises crystallization by mixing with a solvent, evaporation, washing with a second solvent, and vacuum drying. In some embodiments, acid cannabinoids are purified by crystallization.

Methods described herein can further comprise one or more decarboxylation steps. In some embodiments, the decarboxylation step is performed in order to convert cannabinoid acids to their corresponding neutral cannabinoids. In some embodiments, the decarboxylation step is performed by heating one or more cannabinoids for a length of time at a temperature, e.g., heating one or more cannabinoids for at least 1 hour, at least 2 hours, at least 3 hours, at least 4 hours, at least 5 hours, at least 6 hours, at least 7 hours, at least 8 hours or more at about 60° C., about 70° C., about 80° C., about 90° C., about 100° C., about 110° C., about 120° C., about 130° C., about 140° C., about 150° C., about 160° C., about 170° C., about 180° C., or more.

Methods described herein can further comprise one or more decolorization steps. In some embodiments, the decolorization step is performed in order to remove chlorophyll and unwanted pigments. The decolorization step can be performed before and/or after extraction, e.g., performed on cannabis plant material and/or cannabinoid preparations. In some embodiments, the decolorization step includes treatment with activated carbon, or metal salts such as stannous chloride.

Methods described herein can further comprise one of more concentration steps. In some examples, one or more cannabinoids are concentrated after performing an aqueous base extraction. In some embodiments, the concentration step can be performed by precipitation followed by sedimentation, filtration, centrifugation, or any combination. In some embodiments, the concentration step can be performed by subjecting the aqueous solution with precipitated cannabinoids to a freeze thaw cycle, before or after, a primary concentration step has been performed. The freeze thaw cycle enhances the concentration step by removing the precipitate from the aqueous solution. Alternatively, or in addition to, one or more cannabinoids can be concentrated after performing a purification step.

Methods described herein provide high efficiency removal of cannabinoids from cannabis plant material. For example, methods described herein provide removal of greater than 50% of cannabinoids from cannabis plant material, e.g., greater than 60%, greater than 70%, greater than 80%, greater than 90%, greater than 95%, or more of cannabinoids can be removed from cannabis plant material using methods described herein.

Methods described herein can produce highly pure cannabinoids. For example, experiments with the methods described herein produced cannabinoids having a total cannabinoid purity greater than 92% weight percent (e.g., greater than 93%, greater than 94%, greater than 95%, greater than 96%, greater than 97%, greater than 98%, greater than 99%, greater than 99.5% or more).

COMPOSITIONS AND USES

Aspects of the present disclosure provide compositions comprising cannabinoids produced according to methods described herein. Any of the one or more cannabinoids extracted and purified as described herein can be included in a composition.

In some embodiments, the composition includes a cannabinoid-amine salt. Non-limiting examples of cannabinoid-amine salts include cannabinoid-dimethylethanolamine (DMEA) salts (e.g., THCA-DMEA), cannabinoid-dicyclohexylamine salts (e.g., THCA-dicyclohexylamine), cannabinoid-piperidineethanol salts (e.g., THCA-piperidineethanol), cannabinoid-tetramethylethylenediamine (TMEDA) salts (e.g., THCA-TMEDA), cannabinoid-1,8-diazabicyclo [5.4.0]undec-7ene (DBU) salts (e.g., THCA-DBU), cannabinoid-1,5-diazabicyclo[4.3.0]non-5-ene (DBN) salts (e.g., THCA-DBN), cannabinoid-1,4-diazabicyclo[2.2.2]octane (DABCO) salts (e.g., THCA-DABCO), cannabinoid-N,N-diisopropylethylamine salts (e.g., THCA-N,N-diisopropylethylamine), and cannabinoid-quinine salts (e.g., THCA-quinine).

Compositions described herein can include various ratios of cannabinoid to amine. In some embodiments, the composition can include 1:1 to 40,000:1 cannabinoid:amine, e.g., 2:1, 5:1, 10:1, 50:1, 100:1, 500:1, 1,000:1, 5,000:1, 10,000:1, 20,000:1, or 30,000:1.

Cannabinoids produced as described herein can be used in any downstream application of cannabinoids including, but not limited to, pharmaceutical uses. Accordingly, the present disclosure encompasses compositions comprising one or more cannabinoids produced as described herein and uses of such compositions.

Any of the one or more cannabinoids extracted and purified as described herein can be mixed with a pharmaceutically acceptable excipient (carrier) to form a pharmaceutical composition for use in treating a disease (e.g., pain anxiety or panic, depression, inflammation, neurodegenerative disease, arthritis, nausea, anorexia, epilepsy, spasticity, and combinations thereof). “Acceptable” means that the excipient must be compatible with the one or more cannabinoids (and preferably, capable of stabilizing the one or more cannabinoids) and not deleterious to the subject to be treated. Pharmaceutically acceptable excipients (carriers), including buffers, are well known in the art. See, e.g., Remington: The Science and Practice of Pharmacy $20^{th}$ Ed. (2000) Lippincott Williams and Wilkins, Ed. K. E. Hoover.

EMBODIMENTS

Embodiment 1 is a method for aqueous extraction of cannabinoids from cannabis plant, the method comprising (a) contacting cannabis plant material with an aqueous base solution for a time and under conditions sufficient for extraction of one or more cannabinoids from the cannabis plant material into the aqueous base solution; (b) collecting the aqueous base solution comprising the one or more cannabinoids; (c) adding an aqueous amine solution to the aqueous base solution to produce one or more acidic cannabinoid-amine salts.

Embodiment 2 is the method of embodiment 1, wherein the ratio of cannabis plant material and the aqueous base solution is between 1:2 to 1:20 (w/v).

Embodiment 3 is the method of embodiment 2, wherein the ratio of cannabis plant material and the aqueous base solution is 1:10 (w/v).

Embodiment 4 is the method of any one of embodiments 1-3, wherein the aqueous base solution is selected from the group consisting of an aqueous sodium hydroxide solution, an aqueous potassium hydroxide solution, an aqueous calcium hydroxide solution, an aqueous ammonium hydroxide solution, an aqueous sodium bicarbonate solution, an aqueous potassium bicarbonate solution, an aqueous sodium carbonate solution, and an aqueous potassium carbonate solution.

Embodiment 5 is the method of embodiment 4, wherein the aqueous base solution is the aqueous sodium hydroxide solution.

Embodiment 6 is the method of any one of embodiments 1-5, wherein the concentration of the aqueous base solution is between 0.1 to 0.6 M.

Embodiment 7 is the method of embodiment 6, wherein the concentration of the aqueous base solution is 0.3 M.

Embodiment 8 is the method of any one of embodiments 1-7, wherein steps (a) and (b) are repeated from 2 to 6 times using fresh aqueous base solution.

Embodiment 9 is the method of any one of embodiments 1-8, wherein the aqueous amine solution is selected from the group consisting of an aqueous dimethylethanolamine (DMEA) solution, an aqueous dicyclohexylamine solution, an aqueous piperidineethanol solution, an aqueous tetramethylethylenediamine (TMEDA) solution, an aqueous 1,8-diazabicyclo[5.4.0]undec-7ene (DBU) solution, an aqueous 1,5-diazabicyclo[4.3.0]non-5-ene (DBN) solution, an aqueous 1,4-diazabicyclo[2.2.2]octane (DABCO) solution, an aqueous N,N-diisopropylethylamine solution, and an aqueous quinine solution.

Embodiment 10 is the method of any one of embodiments 1-9, further comprising (c) adding an aqueous acid solution to the aqueous base solution to produce a precipitate comprising the one or more cannabinoids; and (d) collecting the precipitate comprising the one or more cannabinoids.

Embodiment 11 is the method of embodiment 10, wherein the aqueous acid solution is added to the aqueous base solution in an amount sufficient to adjust the pH to between 4.5 and 1.5.

Embodiment 12 is the method of embodiment 10 or embodiment 11, wherein the aqueous acid solution is selected from the group consisting of an aqueous hydrochloric acid solution, an aqueous sulfuric acid solution, and an aqueous formic acid solution.

Embodiment 13 is the method of any one of embodiments 10-12, wherein, prior to step (c), the aqueous base solution is centrifuged, filtered, or both centrifuged and filtered.

Embodiment 14 is the method of any one of embodiments 10-13, wherein the precipitate comprising the one or more cannabinoids is collected by centrifugation, filtration, or both centrifuged and filtered.

Embodiment 15 is the method of any one of embodiments 10-14, further comprising (e) dissolving the precipitate comprising the one or more cannabinoids in an ethanol solution and purifying the one or more cannabinoids from the ethanol solution.

Embodiment 16 is the method of embodiment 15, wherein the one or more cannabinoids are purified from the ethanol solution by evaporation, distillation, hydrophobic affinity chromatography, or a combination thereof.

Embodiment 17 is the method of embodiment 16, wherein the hydrophobic affinity chromatography is performed using a polydivinylbenzene resin.

Embodiment 18 is a method for continuous aqueous extraction of cannabinoids from cannabis plant, the method comprising circulating an aqueous base solution between a first stirred-tank reactor and a second stirred-tank reactor, wherein the first stirred-tank reactor comprises cannabis plant material and the second stirred-tank reactor comprises a hydrophobic chromatography resin, and wherein the aqueous base solution is circulated for a time and under conditions sufficient for extraction of one or more cannabinoids from the cannabis plant material into the aqueous base solution and for the one or more cannabinoids in the aqueous base solution to bind to the hydrophobic chromatography resin.

Embodiment 19 is the method of embodiment 18, wherein the ratio of cannabis plant material and the aqueous base solution is between 1:2 to 1:20 (w/v).

Embodiment 20 is the method of embodiment 19, wherein the ratio of cannabis plant material and the aqueous base solution is 1:10 (w/v).

Embodiment 21 is the method of any one of embodiments 18-20, wherein the aqueous base solution is selected from the group consisting of an aqueous sodium hydroxide solution, an aqueous potassium hydroxide solution, an aqueous calcium hydroxide solution, an aqueous ammonium hydroxide solution, an aqueous sodium bicarbonate solution, an aqueous potassium bicarbonate solution, an aqueous sodium carbonate solution, and an aqueous potassium carbonate solution.

Embodiment 22 is the method of embodiment 21, wherein the aqueous base solution is the aqueous sodium hydroxide solution.

Embodiment 23 is the method of any one of embodiments 18-22, wherein the concentration of the aqueous base solution is between 0.1 to 0.6 M.

Embodiment 24 is the method of embodiment 23, wherein the concentration of the aqueous base solution is 0.3 M.

Embodiment 25 is the method of any one of embodiments 18-24, further comprising washing and drying the hydrophobic chromatography resin.

Embodiment 26 is the method of any one of embodiments 18-25, further comprising eluting the one or more cannabinoids from the hydrophobic chromatography resin into an ethanol solution.

Embodiment 27 is the method of embodiment 26, further comprising purifying the one or more cannabinoids from the ethanol solution.

Embodiment 28 is the method of embodiment 27, wherein the one or more cannabinoids are purified from the ethanol solution by acid precipitation, evaporation, distillation, hydrophobic affinity chromatography, or a combination thereof.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Example 1: Development of Base Extraction Conditions

This Example tested a variety of weak and strong bases to determine optimum strength of base needed for extraction of cannabinoids from cannabis plants. Tested bases included NaOH, KOH, $Ca(OH)_2$, $NH_4OH$, and $NaHCO_3$. It was determined that all bases except for NaHCO3 could be used to extract cannabinoids. Due to ease of use, NaOH and KOH were used for the majority of further experiments. Both mono or divalent strong bases were effective in extracting cannabinoids from cannabis plants.

Concentration Selection: NaOH and KOH solutions having concentrations ranging from 0M to 2M were prepared and tested for their ability to solubilize D9THCA and CBDA. Higher concentrations showed faster extractions and higher solubility for metal salts, however, above 0.3M the strong base begins to noticeable degrade D9THCA and to a lesser extent CBDA. Solubility of CBDA is higher than D9THC due to the additional OH moiety in CBD. All forms of cannabinoids were extracted using NaOH and KOH. It was also determined that neutral cannabinoids were removed from the plant to a much less extent during base extraction.

Ratio Determination: The ratio of plant material to aqueous phase was tested using 0.3M NaOH. It was determined that a ratio of 10:1 plant material to aqueous phase was most effective, and that approximately 50% of the cannabinoids are extracted in a single wash, 75% in two washes, 88% in three washes, and >95% in four washes. Four washes allowed for greater the 95% of the starting cannabinoids to be removed from the plant material. It was also found that the residual cannabinoids where not always associated with the plant material, and instead a significant proportion of the residual cannabinoids were trapped in the aqueous phase that had saturated the plant material.

Mixing Time Determination: Greater than 70% of the cannabinoids were extracted from cannabis plant in under 10 minutes with stirring at 100 rpm on an overhead mixer in a simple stirred tank, with 100% solubilization occurring after 20 minutes.

Summary: In a simple stirred tank the following conditions for extraction of plant material were found to be most efficient: 10 L of 0.3M NaOH to 1 Kg of dry flower (or 5 kg wet flower) containing 0.5% to 35% cannabinoids (amount of cannabinoids is not limiting) were used in the extraction. Extraction was performed 4 times for 20 minutes each time with stirring (100 rpm, speed not critical). Washes were pooled. Residual plant material was dried and tested for residual cannabinoids, showing that less than 3% of the starting cannabinoids were available.

Example 2: Base Extraction With Acid Precipitation

In this Example, the base extraction from Example 1 was performed with the pooled washes being acidified with HCl.

The extract started to precipitate at pH 9.3, with full precipitation happening at ~4.5. At pH 4.5, the resulting solution contained a precipitate that does not settle in a flask, and that could be filtered using a 0.22 micron filter to recover the precipitate. It was determined that a pH of <2.0 was necessary for flocking of precipitate, or its complete settling from the solution. This was likely the result of complete hydrogenation of the carboxylic acid moiety. The resulting precipitate was dried and tested. It contained >90% of the extracted cannabinoids, in a black crystalline powder that contained ~50% THCA, 3% THC, 1.5% CBDA, 0.5% CBD, 1% CBGA, and 0% CBN. There was noticeable plant material trapped in the powder.

Example 3: Base Extraction, Filtration, and Acid Precipitation

The extraction method was performed as in Example 2, however, the pooled washes were filtered against a series of different micron filters including 200, 50, 20, 5, 2, 0.5 micron filters. The bulk of plant material was retained on the 200, 50 and 20 micron filters. The resulting solution was cleared of plant material. Upon precipitation the resulting brown powder was shown to contain >90% of the available cannabinoids and to be composed of ~62% THCA, 4% THC, 2% CBD, 0.4% CBD, and 1.1% CBGA.

Example 4: Base Extraction, Filtration, Acid Precipitation, Ethanol filtration, and Solvent Removal The extraction method was performed as in Example 3, however, the resulting brown powder was resuspended in 200 proof ethanol and filtered through a 0.22 micron filter. The ethanol was then removed by evaporation and the resulting light grey powder was shown to contain >80% of available cannabinoids and to be comprised of ~70% THCA, 5% THC, 3% CBDA, 0.3% CBD, and 2% CBGA.

Example 5: Base Extraction, Filtration, Acid Precipitation, Ethanol Filtration, Solvent Removal, and Re-Crystallization The material from Example 4 was attempted to be recrystallized with various solvents with limited success. The resulting light grey powder contained ~20% of starting cannabinoids with a purity of ~75% THCA.

Example 6: Base Extraction, Filtration, Acid Precipitation, Ethanol Filtration, and Distillation The material from Example 4 was dissolved in 85% ethanol, the pH was adjusted to 7.0 with NaOH, and then heated under reflux overnight. In the morning, the ethanol solution was tested, and all cannabinoids had been decarboxylated. The ethanol and water were evaporated, and the resulting oil purified by distillation. The resulting deep red oil contained 68% of the starting cannabinoids with a total cannabinoid content of 92% with 82% D9THC, 5% CBN, 3.8% CBD, and 1.2% CBG.

Example 7: Base Extraction, Filtration, Acid Precipitation, Ethanol Filtration, and Chromatography The material from Example 4 was solubilized in 95% ethanol and pH adjusted to 7.0 and filtered against a 0.22 micron filter. Then the solution was loaded on to a chromatography bed (Purolite PCG600c) at a ratio of 800 g to 6 L of resin. The column was preconditioned with 5 CV of water with 1 g/L NaOH, flow rate was 450 mL/min. The solution was loaded at 50 mL/min, after which the column was flushed with 2 CV of water with 1 g/L NaOH, and then a gradient from 0 to 30% ethanol with water with 1 g/L NaoH was performed over 4 CV where 2 large contaminate peaks were collected. Elution order of cannabinoids were as follows: CBDA, CBGA, CBNA, THCA, CBD, CBG, CBN, and THC. THCA began to elute from the column at 32% ethanol, and was complete off column at 47% ethanol. CBG begins to elute at 51%, CBN at 53%, CBN at 56%, and THC at 57%. The gradient was run to 80% and held till absorbance returns to base line. The chromatography bed was stripped with 100% Ethanol for 2 CV, and a final yellow contaminate was collected. Fractions were pooled and neutral fractions were evaporated, and acid fraction were neutralized to pH 7.0 and diluted to 10% with ethanol. Acid cannabinoids were precipitated from solution and collected by filtration, washed with water 3×, and dried via air or freeze drying. THCA fraction contained >90% of the available THCA at a purity >98%, with 0.4% CBNA.

Alternatively, a step gradient was performed with water containing 1 g/L NaOH, 30% ethanol to wash, 50% ethanol to elute the acid cannabinoid fraction, and 80% ethanol to elute the neutral fraction. The resulting acid fraction contained >94% cannabinoids. The resulting neutral fraction contained >95% neutral cannabinoids.

The chromatography was also performed without NaOH, however, the elution order was CBD, CBDA, CBGA, CBG, CBNA, CBN, THC, and THCA. The gradient was run from 30% to 100%. Under these conditions, the column could not completely resolve THCA from THC.

Finally, the powder from Example 4 was decarboxylated as in Example 6, and the resulting material was run on the column with only the ethanol/water step gradient and no modifiers such as NaOH. The column was washed with 50% ethanol to remove the majority of contaminates. Elution with 80% ethanol resulted in a neutral fraction containing >95% of total loaded cannabinoids with a THC purity of 94%. Running the same material with a gradient from 30% to 80% ethanol over 10 CV resulted in a series of fractions. The THC containing fractions were pooled and the resulting extract contained >85% of the total loaded THC with a purity of 99.2%.

Example 8: Base Extraction, Filtration, Acid Precipitation, Ethanol Filtration, Distillation, and Chromatography Material from Example 6 was dissolved in 200 proof ethanol at a concentration of 300 g/L. Material was loaded on column at a ratio of 800 g/6 L. The column was equilibrated with 5% ethanol in water with no modifiers. The loaded column was washed with 5% ethanol for 4 CV. The column was washed with 50% ethanol for 5 CV to wash off contaminates. Then, the column was eluted with a gradient of 50% to 80% ethanol over 5 CV, thereby eluting all neutral cannabinoids. THC containing fractions were pooled and solvent was evaporated. Resulting residue was 99.4% D9THC, with a 86% yield.

Example 9: Scale up: Base Extraction, Filter Bag Centrifugation, Disk Centrifugation, Acid Precipitation, Disk Centrifugation, Precipitate Drying, Ethanol Filtration, and Chromatography Large scale extraction and purification was performed as described in FIGS. 2A-2B and as follows. In a 800 L stirred tank, 30 kg of dried unground plant material (10% THCA) or 200 kg of wet unground material (2% THCA content) was placed, and the tank was filled to 800 L with 0.3M NaOH at room temperature spared with nitrogen at 8 L/min. The tank was stirred for 1 hour at 150 RPM. The liquid plant slurry was pump at 12 L/min through a Pd800 100 L lifting bag centrifuge with a 100 micron filter bag installed. Liquid was collected and passed through an alpha laval disk centrifuge for fine particle removal at 6 L/min. Cleared liquid was pH adjusted to pH 2.0 with HCl. Precipitate was collected by passing through alpha laval at 6 L/min. Liquid was discarded, and precipitate was dried via forced air drier to a brown powder. Powder was resuspended in 200 proof ethanol and filtered against a 1 micron filter on a vertical stack filter. Ethanol containing ~2700 g of THCA was then loaded on 25 L Millipore vantage A2 column using a Intercem 800 chromatography system. The column contained 12 kg of purolite pcg600. The run conditions for the step gradient are described in Example 7. THC containing fractions were treated with 1 g/L of stannous chloride for reduction of oxidation effects. Ethanol was filtered and removed via evaporation in a rotary evaporator. Resulting oil was pale yellow with D9THC content of 98%. Yield was 67% of starting D9THC.

Figure 3:
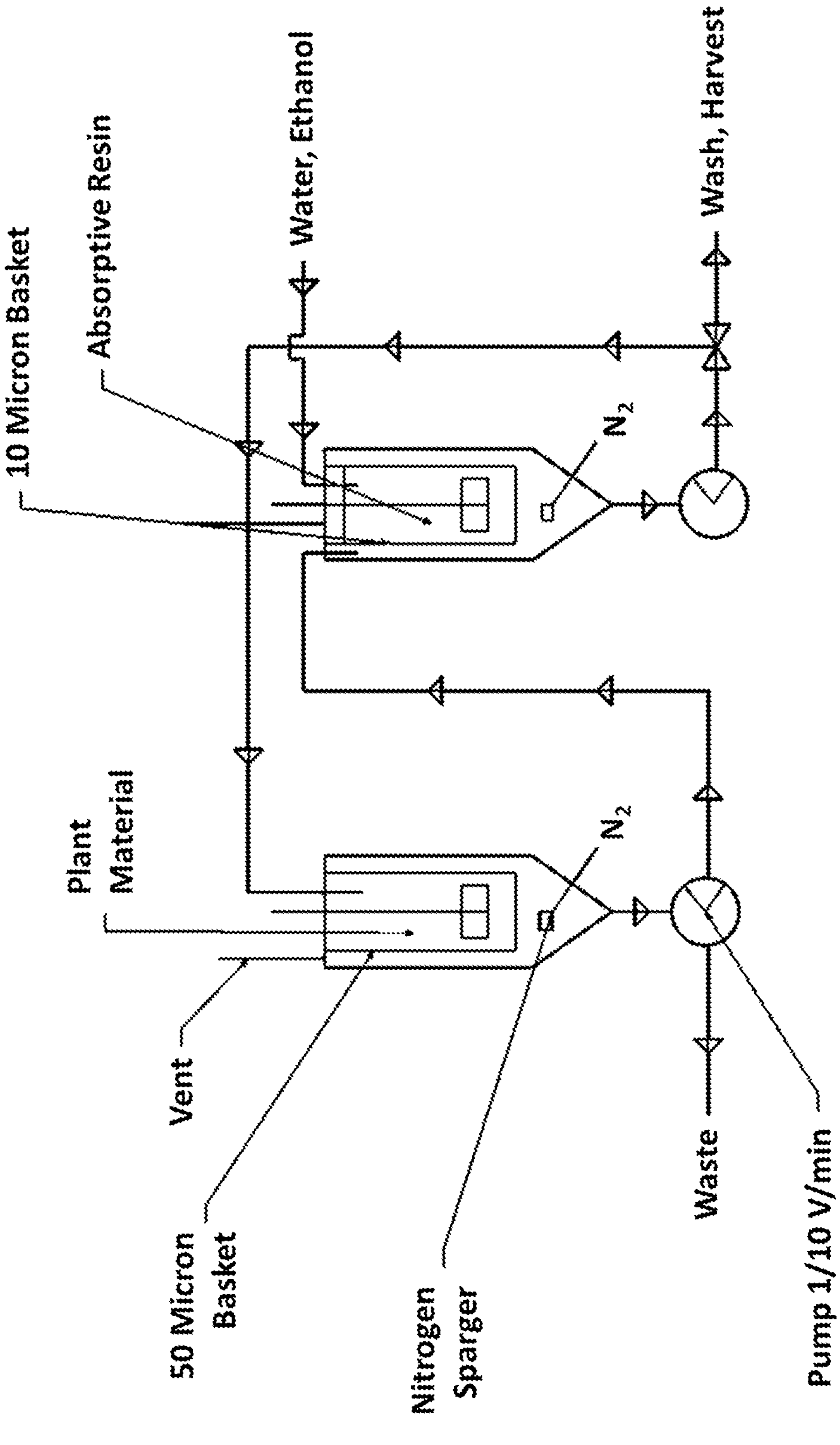
FIG. 3 includes a schematic depiction of a system for ACE in accordance with some embodiments of the technology described herein.

Example 10: Base Extraction with Concurrent Fluidized Bed Absorption, Ethanol Desorption, and Solvent Removal Large scale extraction and purification was performed using the apparatus schematically depicted in FIG. 3. The extraction and purification was performed as follows. In a 200 L conical bottom stirred tank fitted with a 130 L basket made from 50 micron stainless steel mesh, 20 kg of dry or 100 kg wet cannabinoid containing plant material was added inside the basket. In a second 100 L conical bottom stirred tank fitted with a 70 L basket made from 10 micron stainless steel mesh, 40 kg of PCG600C resin was placed inside the basket. A pump capable of 20 L/min was attached via a 2 inch flexible hose to the outlet of the extraction tank and the exit of the pump is place in the space between the edge of basket and the fall of the tank. A second pump was connected to the bottom of the fluidized bed tank and its exit was placed inside the basket of the extraction tank. The system was filled with 250 L of 0.3M NaOH that has been sparged with 2 L/min of $N_2$ for 30 min. Stirring in both tanks was initiated, the pumps were set to 20 L/min and nitrogen was sparged into each tank at a rate of 2 L/min. The aqueous phase was circulated through the plant material, through the 50 micron basket, through the first pump, into the fluidized bed reactor, through the 10 micron screen, and into contact with the absorptive media before leaving the fluidized bed and being returned into the extraction basket. Cannabinoids were extracted from the plant material and carried through the system where the cannabinoids were bound onto the fluidized bed. In 1 hour, >95% of the available cannabinoids have been removed from the plant material and deposited onto the fluidized bed. The pumps were then turned off, the fluidized bed was drained and rinsed with 300 L water at a rate of 10/L min. Vigorous stirring was maintained while the fluidized bed was drained and rinsed. After the bed was washed, it was drained and dried with nitrogen for 1 hour. Following draining and drying, the drained bed was eluted twice with 40 L of 200 proof ethanol. Ethanol was filtered through a 1 micron screen, and removed via rotary evaporation. The resulting material was 84% D9THCA, with a 91% yield.

Example 11: Base Extraction with Concurrent Fluidized Bed Absorption, Ethanol Desorption, Filtration, and Chromatography Instead of being evaporated in a rotary evaporator as described in Example 10, material was loaded onto a 12 L chromatography column. The same chromatography conditions were used as described in Example 7. Resulting D9THCA fractions were pooled, neutralized with HCl, and the resulting precipitate was filtered and washed with neutral water. The resulting bright white powder was 98.3% D9THCA with a >85% yield.

Example 12: Base Extraction with Concurrent Fluidized Bed Absorption, Fractional Ethanol Desorption, Acid Precipitation, and Filtration Using the same apparatus and conditions described in Example 10, a fluidized bed was loaded with THCA. The fluidized bed was washed with 200 L of neutral water. The bed was then drained and dried with nitrogen. Once dry, the bed was washed with 100 L of 33% ethanol containing 1 g/L NaOH. The bed was then eluted with 2×40 L of 47% ethanol containing 1 g/L NaOH. The bed was then striped with 100% ethanol to remove any residual neutral cannabinoids and contaminates. Eluted fractions were pooled and filtered through a 1 micron screen, the pH was adjusted to 2.0 with HCl, and the eluted fractions were diluted in 20% ethanol with water (300 L). The resulting liquid was filtered through a 1 micron screen and the precipitate was collected and resuspended in 5 L of distilled water, frozen and freeze dried. The resulting bright white powder was 92.4% D9THCA with a >90% recovery.

Example 13: Continuous Extraction, Continuous Macro Filtration, Continuous Micro Filtration, Continuous Precipitation, Continuous Precipitation Recovery, and Freeze Drying 200 kg of freshly harvested and bucked cannabis flowers containing an average of 12.8% D9 THCA and 0.14 THC per gram dry weight were fed at 1 kg/min through a 8 foot long, 6 inch diameter screw conveyor run at a slight incline of 10 degrees. An alkali aqueous solution of 0.2 M NaOH was feed through a series of 6 spray ports along the top of the conveyor at a feed rate of 28 L/min (4.66 L/nozzle/min) for approximately 7.5 hours. Plant material was continuously separated from the extraction via a screw press using a 120 micron screen. The resulting post processed plant material had a 50% moisture content and less than 0.2% residual total cannabinoids. The separated alkali extraction fluid containing 1 g/L cannabinoids was continuously passed through a self-cleaning filter with a 20 micron screen at 1 L/min. The filtered extraction fluid was microfiltered via tangential flow filtration against a 1 micron filter, flux rate was set at 1 L/min. Retentate was washed with 0.2M NaOH until no detectable cannabinoid remained, typically less than 3 hold volume washes are necessary to pass all cannabinoids through the filter. Filtrate was then continuously adjusted to pH 2.0 in a flow through cell, and a milky white precipitate formed. Precipitate was concentrated via tangential flow filtration against a 1 micron filler. Precipitate was concentrated to 200 g/L or approximately 55 L, then dia-filtered with water at pH 7 until the retentate pH was 4.5 (typically 6-7 volumes or 385 L was used) and the TFF system was then harvested via air assist. The harvested solution was dewatered on a 1 micron dewatering table with vacuum assist. The resulting white wet precipitate has a moisture content of 50%, cannabinoid content of 38% and contaminate content of 12%. The resulting white wet precipitate was frozen at −20° C. and all remaining water was removed via freeze drying to produce approximately 16 kg of grey to white powder containing 74% acid cannabinoids, 2% neutral cannabinoids, and 24% contaminates. Depending on the desired purity, the material can be further purified via chromatography, distillation, or co-crystallization.

Example 14: Batch Trichrome Mechanical Extraction, Continuous Extraction, Continuous Macro Filtration, Continuous Micro Filtration, Quinine Flocking, Precipitation Recovery, and Freeze Drying 500 kg of freshly harvested and bucked cannabis flowers containing an average of 9.3% D9THCA and 0.11% THC per gram dry weight was mixed with 1500 gallons of water, untreated from municipal sources in a large 2500 gallon stainless steel tank. To this mixture, with agitation via a ribbon impeller, 1000 kg of cubed ice (2 $cm^3$) was added. Agitation was continued, at 75 RPM. After 15 minutes, the water was drained from the tank through a 220 micron metal mesh, leaving the plant material and ice mixture in the tank. The liquid was then passed through a 220 micron vibratory sieve, in line with a 25 micron vibratory sieve. Water was then recycled to the main chilled holding tank, and another 15 minute agitation cycle was started. The process was continued until 4 drain cycles were completed, and water was then allowed to drain to waste instead of draining back to the man tank. At the end of the 4 cycles, any plant material trapped on the 220 micron vibratory sieve was added back to the main tank. Wetted plant material and ice was removed from the tank with inclined screw and passed to the next process step. On the 25 micron vibratory sieve, 6.325 kg of plant material enriched for trichomes of the cannabis plant was recovered. This material, commonly called hash, was then freeze dried at 200 mTorr with a linear temperature ramp from −10° C. to 30° C., over 18 hours. The resulting dried powdery material has a grey to white color, weights 1.55 kg and contains an average THCA content of 61.3% and 7.3% THC and a total terpene content of 8.6%.

The wetted plant material and ice mixture weighting approximately 1400 kg was fed at 3.5 kg/min through an 8 foot long, 6 inch diameter screw conveyor run at a slight incline of 10 degrees. An alkali aqueous solution of 0.4 M NaOH was feed through a series of 6 spray ports along the top of the conveyor at a feed rate of 5.25 L/min (0.875 L/nozzle/min) for approximately 7.0 hours. Plant material and any remaining ice was continuously separated from the extraction via a screw press using a 120 micron screen. The resulting post processed plant material had a 50% moisture content and less than 0.1% residual total cannabinoids.

The separated alkali extraction fluid containing 1.17 g/L cannabinoids was continuously passed through a self-cleaning rotary drum filter with a 75 micron screen at 5.25 L/min. The filtered extraction fluid was microfiltered via tangential flow filtration against a 1 micron filter, flux rate was set at 5.25 L/min. Retentate was washed with 0.2M NaOH until no detectable cannabinoid remained, typically less than 3 hold volume washes are necessary to pass all cannabinoids through the filter.

To the 1 micron filtrate at pH 12.3, a 30% solution of quinine in ethanol was added continuously at a rate of 4.65 ml/min, resulting in a solution that contains 1.4 g/L of quinine and 1.17 g/L THCA. This solution was then continuously adjusted to pH 3.5 in a flow through cell, and a milky white precipitate formed. Solution was allowed to flock for 12 hours in 500 gallon conical bottom tanks. After 12 hours, clarified liquid was decanted and passed through a 1 micron tangential flow filter, concentrating any precipitate that has not flocked. Filter retentate was added to flock from conical tanks. The resulting combined flock had a volume of 52 L, was collected in 55 gallon conical bottom tank, and contains approximately 20% solids. Flock was frozen over night at −4° C., and allowed to thaw for 24 hours. The thawed flock was further dewatered via centrifugation at 3500 rpm for 8 min on a Sorvall™ 12 BP centrifuge, resulting in 20 L of dewatered flock containing 90% solids. The resulting white flocked precipitate was frozen at −20° C. and all remaining water was removed via freeze drying to produce approximately 10 kg of grey to white powder containing 38% acid cannabinoids, 1.7% neutral cannabinoids, 45% quinine, and 15.3% contaminates. Depending on the desired purity, the material can be further purified via chromatography, distillation, or re-crystallization.

Example 15: Continuous Trichrome Mechanical Extraction, Continuous Extraction, Continuous Macro Filtration, Continuous Micro Filtration, Quinine Assisted Flocking, Precipitation Recovery, and Freeze Drying 500 kg of freshly harvested and bucked cannabis flowers containing an average of 9.3% D9THCA and 0.11% THC per gram dry weight was placed on an open top conveyor and conveyed through a liquid nitrogen flash freeze tunnel (Freshline® QS) at 2 kg/min. The flash frozen material was then transferred to an open top vibratory conveyer at 2 kg/min, where it was sprayed with high pressure tap water at 2° C. at 10 L/min. Tap water was contained in a 500 L insulated tank chilled to 2° C. The high pressure tap water dislodges trichomes from the plant material. Water was collected at the bottom of the conveyer, and then passed through a 220 micron vibratory sieve, in line with a 25 micron vibratory sieve. Water was then recycled to a chilled main tank and used in the process again.

On the 25 micron vibratory sieve, 5.84 kg of plant material enriched for trichomes of the cannabis plant are recovered. This material, commonly called hash, is then freeze dried at 200 mTorr with a linear temperature ramp from −10° C. to 30° C., over 18 hours. The resulting dried powdery material has a grey to white color, weights 1.25 kg and contains an average THCA content of 68.3% and 5.3% THC and a total terpene content of 11.6%.

The wetted plant material was further conveyed on a 220 metal mesh, 15 foot long open top conveyor through a series of 6 sprayers where it was treated to high pressure alkali aqueous solution of 0.275 M NaOH. The top of the conveyor at a feed rate of 7.5 L/min (1.25 L/nozzle/min) for approximately 4.5 hours. Plant material and continuously separated from the extraction via a screw press using a 120 micron screen. The resulting post processed plant material had a 50% moisture content and less than 0.1% residual total cannabinoids. The separated alkali extraction fluid containing 2.40 g/L cannabinoids was continuously passed through a self-cleaning rotary drum filter with a 75 micron screen at 7.5 L/min. The filtered extraction fluid was microfiltered via tangential flow filtration against a 1 micron filter, flux rate was set at 7.5 L/min. Retentate was washed with 0.2M NaOH until no detectable cannabinoid remained, typically less than 3 hold up volume washes are necessary to pass all cannabinoids through the filter.

To the 1 micron filtrate at pH 12.3, a 30% solution of quinine in ethanol was added continuously at a rate of 0.75 ml/min, resulting in a solution the solution contains 2.88 g/L of quinine and 2.40 g/L THCA. This solution was then continuously adjusted to pH 3.5 in a flow through cell, and a milky white precipitate formed. Solution was allowed to flock for 12 hours in 500-gallon conical bottom tanks. After 12 hours, clarified liquid was decanted and passed through a 1-micron tangential flow filter, concentrating any precipitate that has not flocked. Concentrated precipitate was added to flock from tanks. The resulting combined flock had a volume of 57 L, was collected in 55 gallon conical bottom tank, and contained approximately 20% solids. Flock was frozen over night at −4° C., and allowed to thaw for 24 hours. The flock was further dewatered via vacuum assisted filtration on a 20 micron filter resulting in 10 L of dewatered flock containing 90% solids. The resulting material is suitable for downstream processing. Alternatively, the resulting white flocked precipitate was frozen at −20° C. and all remaining water was removed via freeze drying to produce approximately 9 kg of grey to white powder containing 39% acid cannabinoids, 1.5% neutral cannabinoids, 46% quinine, and 13.5% contaminates. Depending on the desired purity, the material can be further purified via chromatography, distillation, or re-crystallization.

Example 16: Purification of Crude Acid Cannabinoid Product via Co-crystallization With DHCA 1 kg of material from Example 13 was gently resuspended in 5 L of 200 proof ethanol. The solution was mixed and immediately becomes red-black. The solution was then centrifuged at 7000×g for 5 min. The liquid was removed and 1 L of fresh ethanol was added to the pellet and the process was repeated 5 times. The resulting extracted pellet weighted 138 grams dry, and contained 15.2 grams of cannabinoids. The resulting 10 L of ethanol containing 76 g/L of cannabinoids was then concentrated to 200 g/L cannabinoids via rotary evaporation a 40° C. and 70 mtor, centrifuged a final time for 30 min at 7000×g, and filtered through a 0.22 micron filter.

414 g of dicyclohexylamine (DHCA) was added to the solution (THC-A: DHCA ratio was 1:1.1) and the solution was left at 4° C. for 1 hour, during which a THCA-DHCA precipitate formed. This precipitate was collected via centrifugation at 7000 g and −10° C. for 10 minutes, and was then washed with fresh 200 proof ethanol at −60° C., and collected via centrifugation. Washing was repeated 5 times until the precipitate changed from dark black to bright white. All washes were saved as they contained approximately 50% of the starting cannabinoids. After washing, the precipitate was rinsed with 2 L of −60° C. ethanol over a vacuum assisted 0.22 micron filter at −4° C. in a cold room. The precipitate was then added to 2.5 L of 200 proof room temperature ethanol and incubated at 30° C. for 1 hour, after which the precipitate was fully dissolved. The DHCA was removed by adding 1 kg of Dowex 50WX8 resin (particle size: 200-400 mesh) to the solution with stirring. The ethanol was removed via vacuum filtration, and then passed through a 1 L 50 cm dimeter column containing fresh Dowex resin. The resulting ethanol contained no detectable DHCA. The acid cannabinoids were recovered via removal of the ethanol and drying under vacuum. The resulting bright white powder weighted 346 grams and was 99.8% THCA.

The saved washes were pooled and reconcentrated to 200 g/L THCA, incubated at −10° C., and a THCA-DHCA precipitate was formed. The precipitate was washed and purified as described herein, and a further 173 grams of white precipitate containing 98.7% THCA was recovered.

Finally, washes from the second precipitation were pooled, heated to 30° C., and the residual DHCA removed via Dowex as described herein. This material was then concentrated, decarboxylated, and distilled to produce 179 grams of yellow oil containing 97% THC and 3% minor cannabinoids.

Example 17: Purification of Crude Acid Cannabinoid Product via Co-crystallization With Quinine 1 kg of material from Example 13 was gently resuspended in 3 L of 200 proof ethanol. The solution was mixed on rotary platform for 30 min at 125 rpm, and immediately becomes red-black. The solution was decanted from the solids, and the liquid filtered on a 1 μ m filter disk with vacuum filtration. 2 L of fresh ethanol was added to the solids, and the solution was mixed for 30 min at 200 RPM, and then the liquid was decanted and filtered through a 1 μ m filter disk again. The residual solids are then applied to the filter and the filter cake was rinsed with 2 L of fresh ethanol, for a total of 7 L of ethanol used. The ethanol runs clear at the end of washing. Residual solids were collected from the filter, dried under vacuum, and tested for weight and residual cannabinoids. Solids are 64 g, and cannabinoid content is 0.4%, for a total 256 mg.

The recovered liquid was concentrated at 20 mTorr at 40° C. to 1.5 L total volume, and then 740 grams of anhydrous quinine is added and the total volume product up to 2.25 L. The solution was mixed on a rotating platform at room temperature for 30 minutes, then incubated at −20° C. for 2 hours. After which time a thick precipitate of acid cannabinoid-quinine salt was formed. This precipitate was recovered via vacuum filtration at −5° C. It was then washed with 3×1 L of −80° C. ethanol. The resulting pellet contains 720 grams of THCA. The filtered liquid was saved, concentrated to 500 ml, incubated at −20° C., and a second precipitate recovered, representing a further 16 grams of THCA.

The recovered precipitate was pooled, and dissolved in 5 L of 40° C. acetone, and filtered through a 1 micron filter. The acetone is concentrated to 1.5 L under vacuum at 40° C., incubated for 2 hours at −20° C., and the resulting precipitate collected via filtration, washed with 2×1 L of −20° C. ethanol. The precipitate was the redissolved in 5 L of 40° C. acetone, concentrated to 1.5 L under vacuum at 40° C., incubated for 2 hours at −20° C., and the precipitate was collected via filtration. The collected precipitate was washed with −80° C. ethanol until the ethanol runs clear, typical 3 L total volume. Washes are saved for further purification. The precipitate was dried under vacuum, weighted, and assayed for cannabinoid content. Precipitate was bright white, weights 1264 g and contains 665 g of THCA.

The precipitate was then added to 15 L of 200 proof room temperature ethanol and incubated at 30° C. for 1 hour, with 12 kg of H+ form Dowex 50WX8 resin (particle size: 200-400 mesh) after which the precipitate was fully dissolved, and the quinine is bound to the resin. The ethanol was removed from the resin via vacuum filtration, the resin was washed with 6 L of fresh ethanol, and then passed through a 1 L 50 cm dimeter column containing fresh Dowex resin. The resulting ethanol contained no detectable quinine. The acid cannabinoids were recovered via removal of the ethanol and drying under vacuum. The resulting bright white powder weighed 632 grams and was 99.94% THCA, contains 8.6 ppm of quinine, representing an 85.4% yield.

The saved washes were pooled and concentrated under vacuum at 40° C. to 250 ml. The concentrate was incubated at −20° C. for 2 hours, and the precipitate recovered via filtration. Upon drying it was light brown in color, weighted 112 grams, representing 58 grams of THCA. The precipitate is then saved for inclusion in a new round of purification.

Example 18: Recrystallization of THCA-Quinine Salt 10 kg of material from Example 14 was resuspended in 60 L acetone in a 100 L glass reactor with stirring at 100 RPM at 40° C. The solution was centrifuged to remove solids, via a Sorvall™ 12 BP centrifuge at 4000 RPM for 8 min. The clarified acetone was decanted, and 15 L of fresh acetone was added to the solids, and the solution was mixed for 15 minutes on a shaking platform at 100 RPM and centrifuged again. The 15 L of acetone was decanted and pooled for total volume of 75 L. The residual solids were collected from the centrifuge bottles, dried under vacuum, and tested for weight and residual cannabinoids. Solids were 1020.7 g, and cannabinoid content was 0.6%, for a total 6.12 g.

The recovered acetone was concentrated at 65 mTorr at 40° C. to 20 L total volume, on a 20 L rotary evaporator. The solution was transferred to a 100 L crystallization reactor and further evaporated to 15 L at 40° C. and 85 mTorr, with stirring. After which time a thick precipitate of acid cannabinoid-quinine salt was formed. The precipitate was recovered via vacuum filtration at 40° C. through a 30 micron filter. The precipitate was then washed with 3×3 L of −80° C. 100% ethanol. The resulting pellet contained 3,540 grams of THCA. The filtered liquid was saved, concentrated to 500 mL, incubated at −20° C., and a second precipitate recovered, representing a further 87 grams of THCA.

The washed precipitate was dissolved in 50 L of 40° C. acetone, filtered through a 30 micron filter, and rotovaped down to 20 L at the previous conditions. It was then transferred back to the 100 L reactor, concentrated to 12 L. After which time a thick precipitate of acid cannabinoid-quinine salt was formed. The precipitate was recovered via vacuum filtration at 40° C. through a 30 micron filter. The precipitate was then washed with 3×3 L of −80° C. 100% ethanol. The resulting pellet contains 3,430 grams of THCA. The filtered liquid was saved, concentrated to 500 mL, incubated at −20° C., and a second precipitate recovered, representing a further 110 grams of THCA.

The washed precipitate was dissolved for a final time in 50 L of 40° C. acetone, filtered through a 30 micron filter, and rotovaped down to 20 L at the previous conditions. It was then transferred back to the 100 L reactor, concentrated to 10 L. After which time a thick precipitate of acid cannabinoid-quinine salt was formed. The precipitate was recovered via vacuum filtration at 40° C. through a 30 micron filter. The resulting washed precipitate contains 3355 grams of THCA. The precipitate was then washed with 3×3 L of −80° C. 100% ethanol. The filtered liquid was saved, concentrated to 500 mL, incubated at −20° C., and a second precipitate recovered, representing a further 75 grams of THCA.

The precipitate was resuspended in 10 L of acetone at 40° C., and quinine was removed by the slow addition of 6.82 moles (670 g) of 98% $H_2SO_4$ with stirring. After 30 minutes of stirring a voluminous white precipitate of quinine sulfate was formed and the acetone containing THCA was removed via filtration through a 200 micron filter. The precipitate was then washed with 3×3 L of acetone. Quinine was recovered from the quinine sulfate by adding 10 L of alkaline ethanol containing 1.5 M NaOH. A residue of sodium sulfate was left in the reactor, and it was washed with 2×2 L of ethanol, and the ethanol was filtered through a 30 micron filter. The ethanol contains ~30% quinine and was ready to be reused in the flocking step of the extraction process.

The pooled 16 L of acetone containing 3355 g of THCA was concentrated to dryness on a 20 L rotovap. The resulting bright white precipitate weights 3517 grams and contains 3355 g of THCA, 83 g of THC, 21 g of other cannabinoids, and 53 g of residual quinine.

The precipitate was then added to 15 L of 200 proof room temperature ethanol and incubated at 30° C. for 1 hour, it was then passed through a 10 L column containing 4 kg of H+ form Dowex 50WX8 resin (particle size: 200-400 mesh) with a cap of 100 g of sodium bicarbonate at a rate of 200 ml/min. The column was rinsed with 2×2 L of clean ethanol, until the effluent was clear. The resulting ethanol was free of residual quinine and had a pH of 7.5. The acid cannabinoids were recovered via removal of the ethanol and drying under vacuum. The resulting bright white powder weighed 3460 grams and was 99.8% total cannabinoids (97% THCA, 2.3% THC) contains 1.4 ppm of quinine, representing an 88.2% yield.

Example 18: Composition Comprising Cannabinoids and Quinine

The acid cannabinoids produced from Example 15 represent a new form or preparation of cannabinoids, one which contains a mixture of cannabinoids and quinine. The process in Example 15 can be performed to produce a mixture of THCA and quinine in the ratio of 1:1 molar THCA: quinine to 40,000:1 THCA: quinine. The combination of trace amounts of quinine has antioxidative effects on the cannabinoids, both in the acid and neutral forms. Furthermore, quinine is a MAO competitive inhibitor and its co-administrating with THC may enhance and prolong its effects.

Example 19: Production of Lithium salt of D9THCA or CBDA

Utilizing the process in described in Example 12, LiOH (0.5 g/L) was used instead of NaOH as a modifier in the wash and elution media. Instead of collecting the material via precipitation, the ethanol was removed via evaporation until the material precipitated. The precipitate was filtered and dried as in Example 12. The yield was 93.4% Li-D9THCA at a >90% yield.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for continuous aqueous extraction of cannabinoids from cannabis plant, the method comprising:

circulating an aqueous base solution between a first stirred-tank reactor and a second stirred-tank reactor, wherein the first stirred-tank reactor comprises cannabis plant material and the second stirred-tank reactor comprises a hydrophobic chromatography resin, and wherein the aqueous base solution is circulated for a time and under conditions sufficient for extraction of one or more cannabinoids from the cannabis plant material into the aqueous base solution and for the one or more cannabinoids in the aqueous base solution to bind to the hydrophobic chromatography resin.

2. The method of claim 1, wherein the ratio of cannabis plant material and the aqueous base solution is between 1:2 to 1:20 (w/v).

3. The method of claim 2, wherein the ratio of cannabis plant material and the aqueous base solution is 1:10 (w/v).

4. The method of claim 1, wherein the aqueous base solution is selected from the group consisting of an aqueous sodium hydroxide solution, an aqueous potassium hydroxide solution, an aqueous calcium hydroxide solution, an aqueous ammonium hydroxide solution, an aqueous sodium bicarbonate solution, an aqueous potassium bicarbonate solution, an aqueous sodium carbonate solution, and an aqueous potassium carbonate solution.

5. The method of claim 4, wherein the aqueous base solution is the aqueous sodium hydroxide solution.

6. The method of claim 1, wherein the concentration of the aqueous base solution is between 0.1 to 0.6 M.

7. The method of claim 6, wherein the concentration of the aqueous base solution is 0.3 M.

8. The method of claim 1, further comprising washing and drying the hydrophobic chromatography resin.

9. The method of claim 1, further comprising eluting the one or more cannabinoids from the hydrophobic chromatography resin into an ethanol solution.

10. The method of claim 9, further comprising purifying the one or more cannabinoids from the ethanol solution.

11. The method of claim 10, wherein the one or more cannabinoids are purified from the ethanol solution by acid precipitation, evaporation, distillation, hydrophobic affinity chromatography, or a combination thereof.

* * * * *